United States Patent
Papenfuss

(10) Patent No.: US 10,743,912 B2
(45) Date of Patent: Aug. 18, 2020

(54) SURGICAL TUNNELING INSTRUMENT WITH EXPANDABLE SECTION

(71) Applicant: Lenkbar, LLC, Naples, FL (US)

(72) Inventor: Erik Papenfuss, Naples, FL (US)

(73) Assignee: Lenkbar, LLC, Naples, FL (US)

( * ) Notice: Subject to any disclaimer, the term of this patent is extended or adjusted under 35 U.S.C. 154(b) by 114 days.

(21) Appl. No.: 15/765,330

(22) PCT Filed: Nov. 15, 2016

(86) PCT No.: PCT/US2016/062026
§ 371 (c)(1),
(2) Date: Apr. 2, 2018

(87) PCT Pub. No.: WO2017/087382
PCT Pub. Date: May 26, 2017

(65) Prior Publication Data
US 2018/0280033 A1    Oct. 4, 2018

Related U.S. Application Data

(60) Provisional application No. 62/256,205, filed on Nov. 17, 2015.

(51) Int. Cl.
*A61B 17/34* (2006.01)
*A61B 17/16* (2006.01)
(Continued)

(52) U.S. Cl.
CPC ...... *A61B 17/3417* (2013.01); *A61B 17/0401* (2013.01); *A61B 17/1604* (2013.01);
(Continued)

(58) Field of Classification Search
CPC . A61B 17/16; A61B 17/1604; A61B 17/1613; A61B 17/1615; A61B 17/1617;
(Continued)

(56) References Cited

U.S. PATENT DOCUMENTS

| 3,827,821 A | 8/1974 | Swenson |
| 4,475,852 A | 10/1984 | Koppelmann |

(Continued)

FOREIGN PATENT DOCUMENTS

WO    2014089198 A1    6/2014

OTHER PUBLICATIONS

Extended European Search Report for European Application No. 16 866 945.5, dated May 22, 2019, 5 pages.

(Continued)

*Primary Examiner* — Larry E Waggle, Jr.

(74) *Attorney, Agent, or Firm* — RatnerPrestia

(57) ABSTRACT

A trocar for preparing pilot holes, tunnels and other spaces within bone includes a piercing tip, a cutting element, and an expansion element for expanding the cutting element radially outwardly with respect to a longitudinal axis of the trocar. The cutting element includes one or more cutting blades. The trocar also includes a hollow shaft. The hollow shaft can include one or more apertures axially and radially aligned with the one or more cutting blades. The expansion element can include an activation rod housed inside the hollow shaft. The one or more cutting blades can be in the form of two opposed cutting blades separated by a gap, the two opposed cutting blades being radially displaceable with respect to the longitudinal axis. The activation rod can include a wedge that partially enters the gap between the two opposed cutting blades to displace the cutting blades to an expanded position.

13 Claims, 6 Drawing Sheets

(51) Int. Cl.
*A61B 17/32* (2006.01)
*A61B 17/04* (2006.01)
*A61B 90/00* (2016.01)
*A61B 17/00* (2006.01)

(52) U.S. Cl.
CPC ...... *A61B 17/1615* (2013.01); *A61B 17/1617* (2013.01); *A61B 17/1631* (2013.01); *A61B 17/34* (2013.01); *A61B 17/3472* (2013.01); *A61B 2017/00367* (2013.01); *A61B 2017/0409* (2013.01); *A61B 2017/320056* (2013.01); *A61B 2090/0807* (2016.02)

(58) Field of Classification Search
CPC ........ A61B 17/1631; A61B 17/320725; A61B 2017/320056; A61B 17/34; A61B 17/3417; A61B 17/3472; B23B 29/03446
See application file for complete search history.

(56) References Cited

U.S. PATENT DOCUMENTS

| | | | |
|---|---|---|---|
| 4,635,737 A * | 1/1987 | Miyanaga | B23B 51/0045 175/284 |
| 5,342,365 A * | 8/1994 | Waldman | A61B 17/1659 407/29.1 |
| 5,443,475 A | 8/1995 | Auerbach et al. | |
| 5,445,639 A | 8/1995 | Kuslich et al. | |
| 6,740,090 B1 | 5/2004 | Cragg et al. | |
| 7,179,024 B2 | 2/2007 | Greenhalgh | |
| 7,429,264 B2 | 9/2008 | Melkent et al. | |
| 7,828,804 B2 | 11/2010 | Li et al. | |
| 7,892,235 B2 * | 2/2011 | Ellis | B23B 51/00 606/80 |
| 8,246,627 B2 | 8/2012 | Vanleeuwen et al. | |
| 8,343,158 B2 | 1/2013 | Birkbeck | |
| 9,364,259 B2 | 6/2016 | Lunsford et al. | |
| 9,517,076 B2 | 12/2016 | Papenfuss | |
| 9,655,629 B2 | 5/2017 | Takeuchi | |
| 9,668,750 B2 | 6/2017 | Mirochinik et al. | |
| 9,668,751 B2 | 6/2017 | Papenfuss | |
| 9,795,395 B2 | 10/2017 | Lizardi et al. | |
| 10,448,959 B2 * | 10/2019 | Slobitker | A61B 17/1617 |
| 2004/0208717 A1 | 10/2004 | Greenhalgh | |
| 2005/0096685 A1 | 5/2005 | Murphy et al. | |
| 2005/0113836 A1 | 5/2005 | Lozier et al. | |
| 2005/0277971 A1 | 12/2005 | Melkent et al. | |
| 2006/0241629 A1 | 10/2006 | Krebs et al. | |
| 2007/0123889 A1 | 5/2007 | Malandain et al. | |
| 2007/0282345 A1 | 12/2007 | Yedlicka et al. | |
| 2008/0114364 A1 | 5/2008 | Goldin et al. | |
| 2008/0221608 A1 | 9/2008 | Betts | |
| 2008/0294168 A1 | 11/2008 | Wieland | |
| 2010/0094296 A1 | 4/2010 | Birkbeck | |
| 2010/0268175 A1 | 10/2010 | Lunsford et al. | |
| 2011/0130760 A1 | 6/2011 | Anderson et al. | |
| 2011/0251616 A1 | 10/2011 | Osman et al. | |
| 2012/0022568 A1 | 1/2012 | Koblish et al. | |
| 2013/0165935 A1 | 6/2013 | Griffiths et al. | |
| 2013/0340240 A1 | 12/2013 | Irawan | |
| 2014/0257297 A1 | 9/2014 | Koogle et al. | |
| 2015/0313611 A1 * | 11/2015 | O'Farrill | A61B 17/1617 606/80 |
| 2017/0143352 A1 | 5/2017 | Papenfuss | |

OTHER PUBLICATIONS

Non Final Office Action for U.S. Appl. No. 15/357,373, dated Jun. 3, 2019, 23 pages.
Notice of Allowance for U.S. Appl. No. 15/357,373, dated Sep. 26, 2019, 11 pages.
International Search Report and Written Opinion for International Application No. PCT/US2016/062026, dated Feb. 16, 2017, 6 pages.
International Preliminary Report on Patentability for International Application No. PCT/US2016/062026, dated May 22, 2018, 6 pages.
Australian Examination Report for Australian Application No. 2016355390, dated Sep. 24, 2018, 3 pages.

* cited by examiner

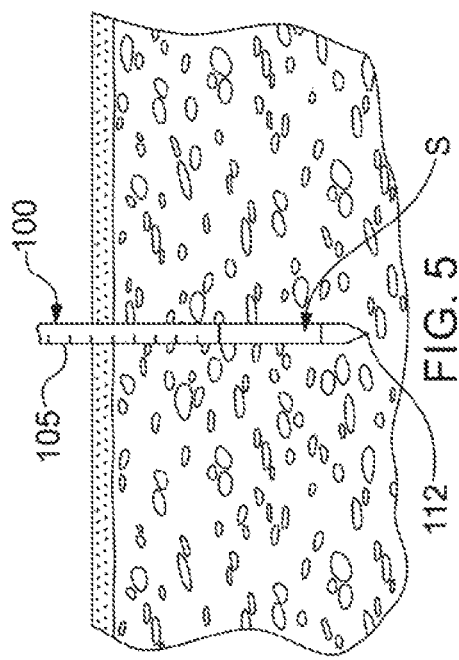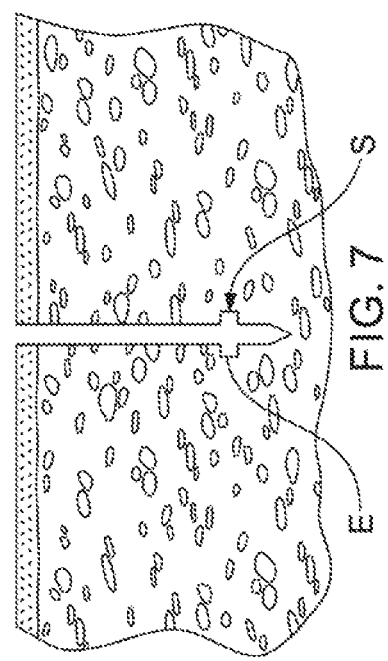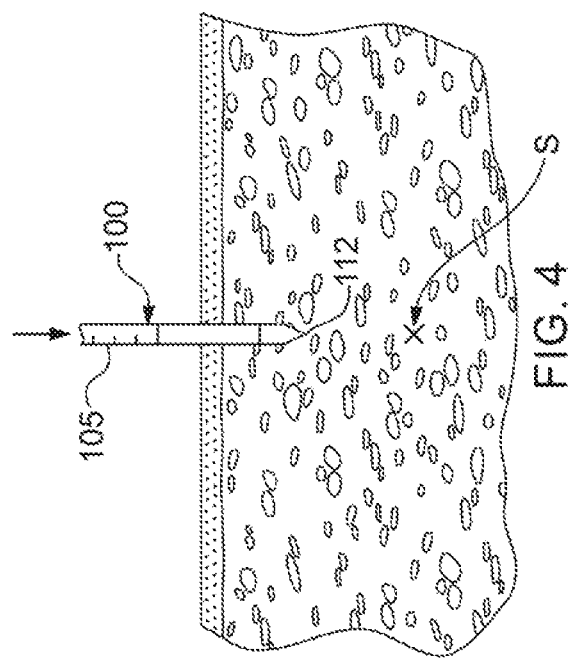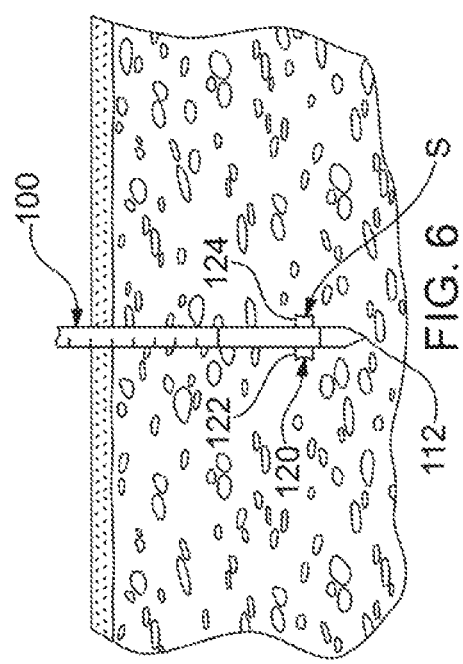

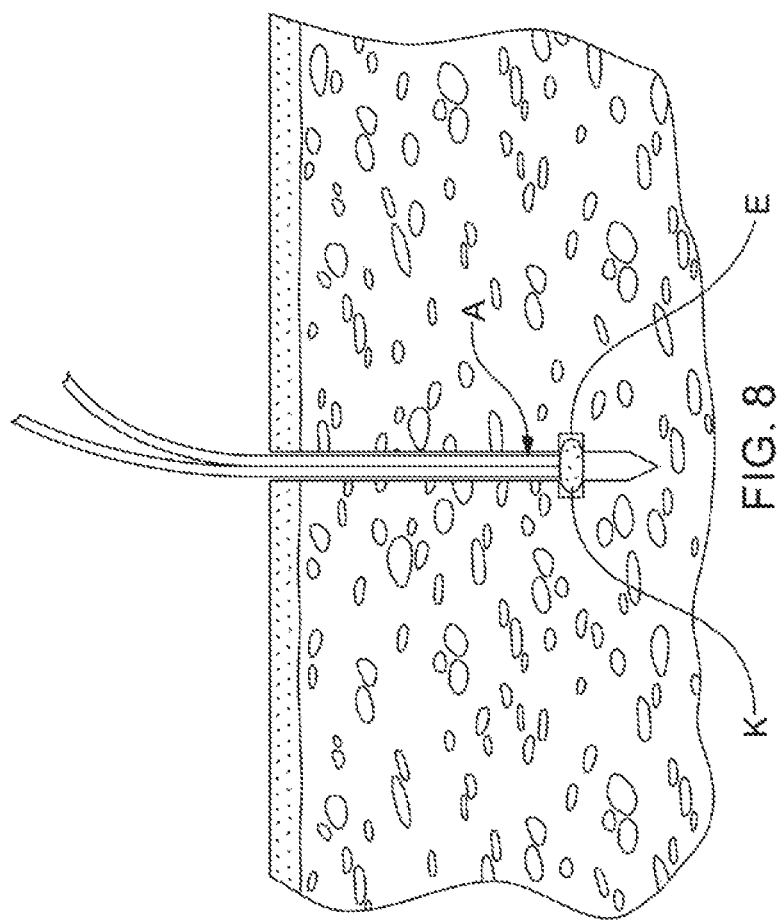

SURGICAL TUNNELING INSTRUMENT WITH EXPANDABLE SECTION

RELATED APPLICATION(S)

This application is the United States national phase entry of International Application No. PCT/US2016/062026, filed Nov. 15, 2016, which is related to and claims the benefit of priority of U.S. Provisional Application Ser. No. 62/256,205, filed Nov. 17, 2015. The contents of International Application No. PCT/US2016/062026 and U.S. Provisional Application Ser. No. 62/256,205 are incorporated by reference herein in their entireties.

FIELD

The present invention relates generally to surgical instruments for preparing pilot holes, tunnels and the like in bone, and more specifically to a surgical trocar with an expandable element for preparing a bony tunnel with an enlarged section at a selected location within the bony tunnel.

BACKGROUND

In rotator cuff repair and other surgical procedures, tendons or tissues that are separated from bone can be attached and secured to the bone with one or more tissue anchors. Tissue anchors can include a bone anchor portion that attaches to a bone, and one or more sutures that connect with the tissue being secured. The bone anchor portion can be secured to the inside of a pilot hole, tunnel or other opening formed in the bone.

There are different types of tissue anchors available. Some tissue anchors feature a bone anchor portion having a threaded or non-threaded body that is driven or tapped into a hole in the bone. Other types include "all-suture anchors", which are made up of sutures that are anchored in the hole in the bone. Some all-suture anchors have sutures that are looped so that the sutures form a large knot after the sutures are advanced into a hole and pulled in tension. The cross-sectional footprint of the knot is larger than the cross-sectional area of the hole, allowing the knot to bear again the wall of the hole in a form fit. The pull-out strength of form fit knots in bony tunnels can vary. Inadequately secured knots pose a risk that the knot can be pulled out of the tunnel, causing detachment of the tissue anchor from the bone, and subsequent need for revision surgery and repair.

SUMMARY

Applicant has developed a surgical instrument for improving the retention of tissue anchors in bone. In one embodiment, the surgical instrument features a trocar for creating a bony tunnel with improved characteristics for retaining tissue anchors, including all-suture anchors. The trocar includes a shaft with a sharp piercing tip that can be tapped into bone in an axial direction to create the bony tunnel. In addition, the trocar includes a cutting element that works in a radial direction to enlarge the cross section of the tunnel at a specific location or locations. The enlarged cross section creates an enlarged space, void or counterbore within the tunnel that can receive a portion of an all-suture anchor, and in particular the knot being formed by the all-suture anchor as the all-suture anchor is deployed in the tunnel.

Cutting elements in accordance with the invention can create an enlarged tunnel cross section below the bone surface. The proximal end of the enlarged cross section is characterized by a "step" where the tunnel transitions from a larger cross section (i.e. the area cut by the cutting element), to a smaller cross section (i.e. the area formed by the piercing tip by not cut by the cutting element). The size and manner of operating the cutting element can be selected and controlled so that the area of the enlarged cross section is roughly equal to or slightly smaller than the knot to be formed by the all-suture anchor. The size and manner of operating the piercing tip can also be selected and controlled so that the area of the smaller cross section is significantly smaller than the cross section of the knot to be formed. In this arrangement, the step forms a constriction at the proximal end of the enlarged void. The constriction traps the knot in the enlarged void, preventing the knot from slipping or moving along the tunnel. The knot is therefore immobilized in the enlarged void, which secures the all-suture anchor firmly in the bone.

In use, the piercing tip forms a bony tunnel of uniform cross section. The tunnel can be formed by tapping or by drilling depending on the type of tip being used. During advancement of the tip, the cutting element is retracted with respect to the piercing tip. That is, the cutting element is positioned so that the blades are confined to an area completely within the cross sectional shape or footprint of the trocar tip. Once the tunnel is formed to an appropriate depth, the cutting element can be expanded and deployed to form an enlarged section in the tunnel. The axial position of the cutting element can be carefully monitored within the tunnel so that an enlarged section is cut or reamed at a precise location or depth within the tunnel. The cutting element can be used both in an anterograde and retrograde manner to form an enlarged section. Moreover, the location or depth of the enlarged section, and the length of the enlarged section, can be selected to accommodate a particular bone anchor.

The cutting element is fully integrated in the trocar shaft and travels with the shaft during formation of the tunnel. Therefore, the initial tunnel formation, and subsequent cutting of the enlarged section, can be achieved with a single instrument. This avoids the need for cleaning and preparing multiple instruments for the procedure. By preparing a tunnel having a majority of its length limited to a small cross section, and only a small portion having the larger cross section, the tunnel allows the practitioner to take advantage of the benefits of smaller and less invasive holes, which make all-suture anchors desirable, while also utilizing a cut out with larger cross section to improve retention of the bone anchor portion of the tissue anchor.

Instruments for providing the above benefits can be provided in various embodiments in accordance with the invention as will be described herein, any of which can be the subject of the claims.

In one aspect of the invention, an instrument is provided in the form of a trocar featuring a piercing tip, a cutting element, and an expansion element for expanding the cutting element radially outwardly with respect to a longitudinal axis of the trocar.

In another aspect of the invention, a trocar is provided with a cutting element that includes one or more cutting blades.

In another aspect of the invention, a trocar is provided with a hollow shaft.

In another aspect of the invention, the hollow shaft can include one or more apertures axially and radially aligned with one or more cutting blades.

In another aspect of the invention, the cutting element is at least partially housed in a hollow shaft.

In another aspect of the invention, the expansion element includes an activation rod.

In another aspect of the invention, an activation rod is housed inside the hollow shaft in a position proximal to the cutting element.

In another aspect of the invention, a trocar features two opposed cutting blades separated by a gap, the two opposed cutting blades being radially displaceable with respect to the longitudinal axis of the trocar.

In another aspect of the invention, the two opposed cutting blades are radially displaceable away from one another to an expanded position outside of the footprint of the piercing tip, and radially displaceable toward one another to a retracted position inside the footprint of the piercing tip.

In another aspect of the invention, the two cutting blades are biased toward the retracted position.

In another aspect of the invention, the activation rod includes a wedge configured to at least partially enter the gap between the two opposed cutting blades to displace the cutting blades to the expanded position.

In another aspect of the invention, the activation rod is axially displaceable in the hollow shaft between a distal position, in which the activation rod engages and radially displaces the two opposed cutting blades to the expanded position, and a proximal position, in which the opposed cutting blades are displaced to the retracted position.

In another aspect of the invention, each of the cutting blades comprises a cutting face.

In another aspect of the invention, each cutting face comprises a concave-shaped face.

In another aspect of the invention, each cutting face comprises a C-shaped face.

In another aspect of the invention, each cutting face comprises a V-shaped face.

In another aspect of the invention, each cutting face comprises a pair of cutting teeth.

In another aspect of the invention, each of the cutting teeth defines an edge that extends parallel to the longitudinal axis of the trocar.

In another aspect of the invention, each of the cutting teeth defines an edge that extends perpendicularly to the longitudinal axis of the trocar.

In another aspect of the invention, the hollow shaft comprises an end for attaching the trocar to a device for providing torque.

BRIEF DESCRIPTION OF THE DRAWINGS

The foregoing summary and the following detailed description will be better understood with the non-limiting examples shown in the accompanying drawings, which are not to scale, of which:

FIG. 4 is a schematic view illustrating a step for forming a bony tunnel in accordance with one possible instrument and method of the invention;

FIG. 5 is a schematic view illustrating another step for forming a bony tunnel in accordance with one possible instrument and method of the invention;

FIG. 6 is a schematic view illustrating another step for forming a bony tunnel in accordance with one possible instrument and method of the invention;

FIG. 7 is a schematic view of one possible bony tunnel that can be formed in accordance with one possible instrument and method of the invention;

FIG. 8 is a schematic view of one possible tissue anchor secured in the bony tunnel of FIG. 7.

DETAILED DESCRIPTION

Figure 1:
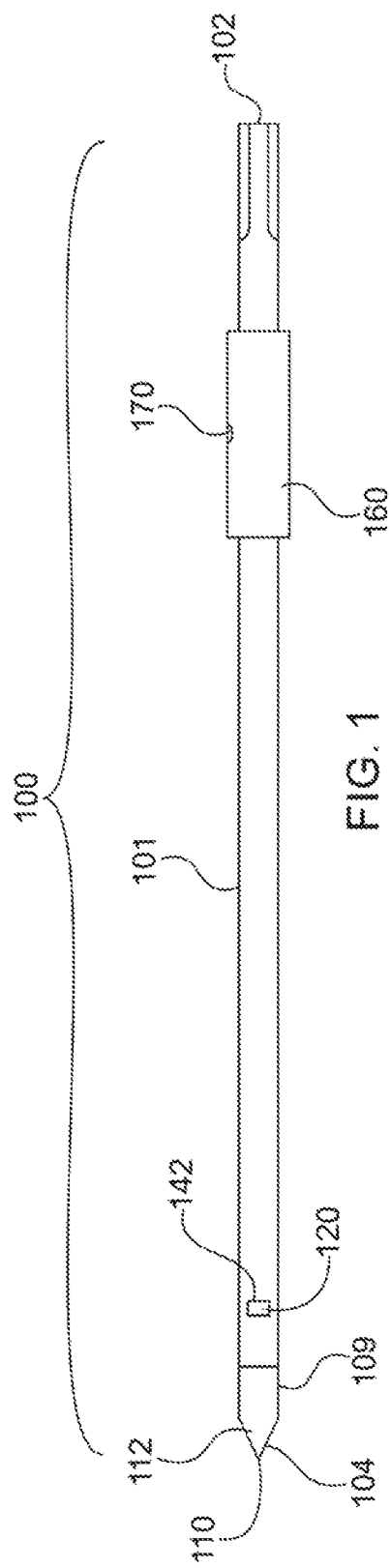
FIG. 1 is a side view of an instrument in accordance with the invention, in the form of a trocar.
Figure 2:
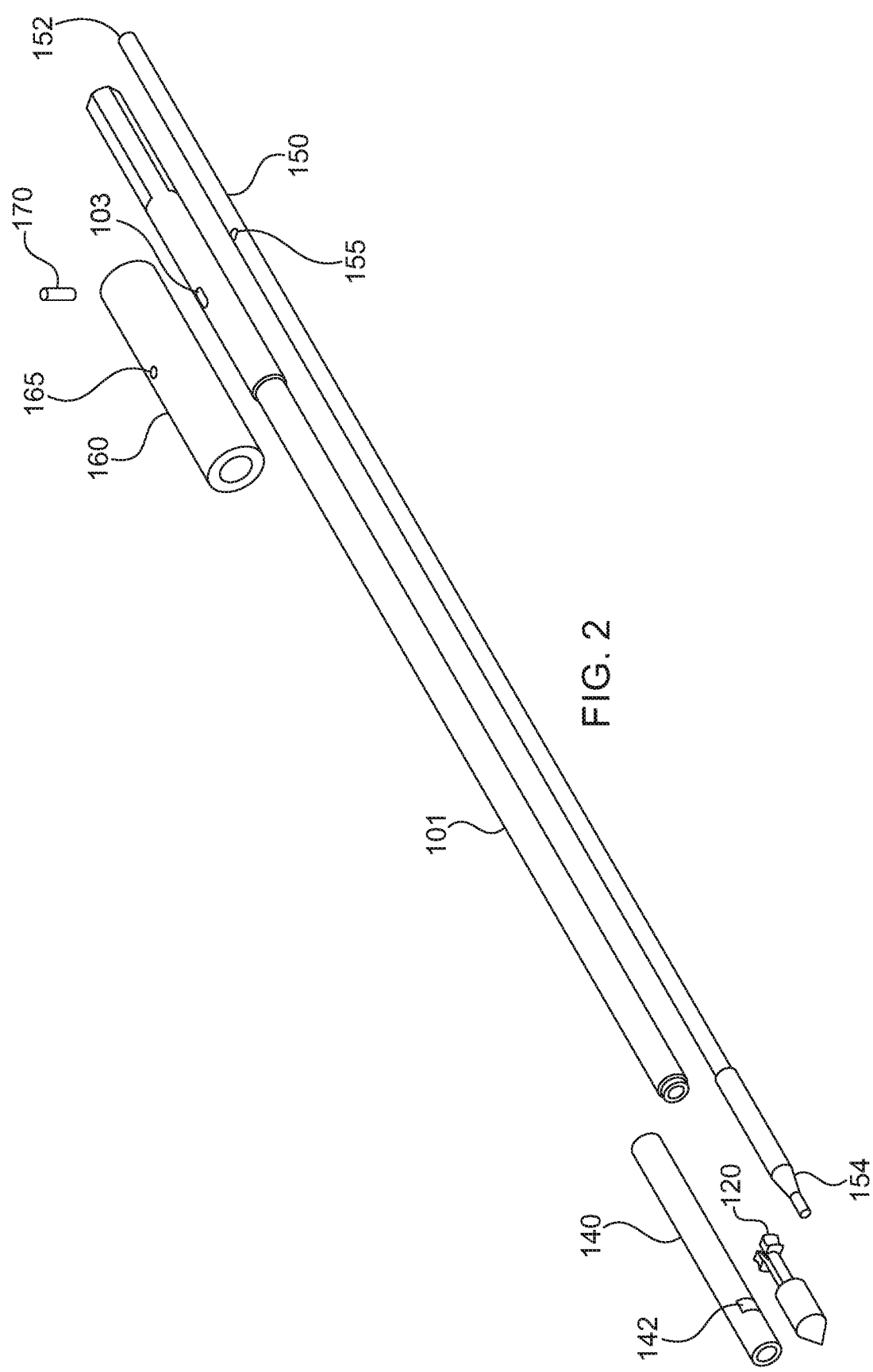
FIG. 2 is an exploded perspective view of the instrument of FIG. 1.
Figure 3:
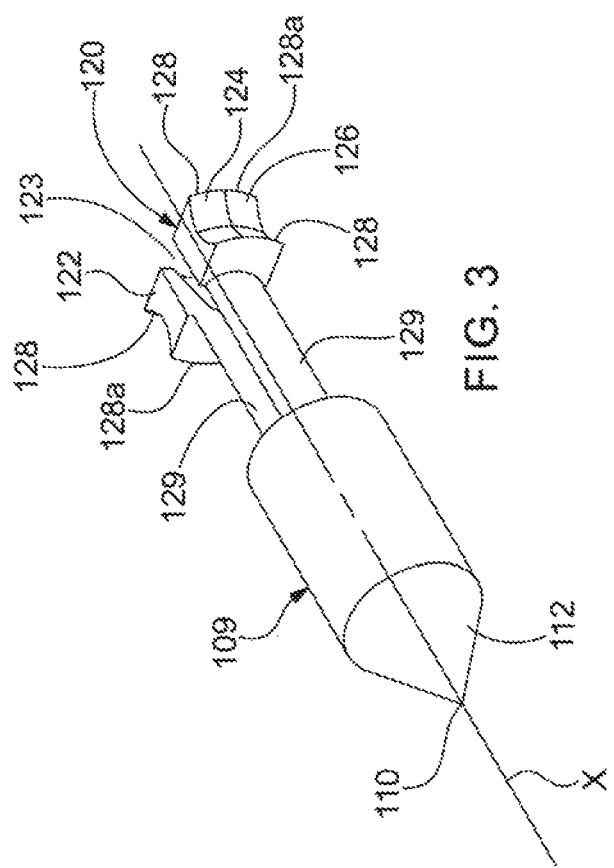
FIG. 3 is an enlarged view of one of the components of FIG. 2.

Referring to FIGS. 1-3, an instrument in the form of a trocar 100 is shown in accordance with a first embodiment of the invention. Trocar 100 has a proximal end 102, a distal end 104 and a sharpened end 110 at the distal end. Sharpened end 110 is shown in the form of a sharp piercing tip 112 that is solid or non-cannulated. Trocar 100 also has a trocar head 109 that includes the sharp piercing tip 112. Trocar heads in accordance with the invention can feature a solid sharpened piercing tip like sharp piercing tip 112. Alternatively, trocar heads in accordance with the invention can feature a blunt tip, a hollow tip, or a drill bit. Regardless of the configuration, trocars in accordance with the invention are designed to create a small diameter tunnel in bone. The tunnel can be formed by punching or driving the distal end of the trocar through cortical bone and into cancellous bone.

Trocar heads in accordance with the invention also include a cutting element for cutting an enlarged section in a tunnel during or after formation of the tunnel. The cutting element can be deployed with an expansion element that is operable to expand the cutting element radially outwardly with respect to a longitudinal axis X of the trocar head. Trocar heads and cutting elements can be coupled to a device for providing torque, to rotate the trocar head and cutting element in order to cut an enlarged section in a tunnel. For example, a surgical drill, driver or other source of torque can be attached to proximal end 102 of trocar 100 to rotate the cutting element to cut the enlarged section in the tunnel. In this regard proximal end 102 can include beveled or flattened sections that allow a drill, driver or other tool to be clamped to the trocar 100 using a chuck or other known attachment mechanism.

Cutting elements in accordance with the invention can take various forms, including one or more blades or blade sections that project radially outwardly from the trocar head. For example, trocar head 109 features a cutting element 120 that is provided in the form of one or more blades, and more specifically, two opposing blades comprised of a first blade 122 and a second blade 124. Each of blades 122 and 124 features a concave cutting face, and in particular a C-shaped cutting face 126. Each cutting face 126 comprises cutting teeth 128 that can cut radially outwardly as well as in an axial direction. Each cutting tooth 128 defines a linear or substantially linear edge 128a that extends perpendicularly to longitudinal axis X of trocar head 109. With regard to axial cutting, the teeth 128 can cut both in a proximal direction and distal direction. The C-shaped profile of cutting face 126 cuts only a small surface area of the tunnel wall, so there is less surface area to cut. This creates less resistance at the beginning of the cut to make the start of cutting easier. The C-shaped profile also makes it easier to radially expand the cutting face into the bone during cutting, when cutting an enlarged diameter section.

It will be understood that the cutting elements in accordance with the invention can consist of a single cutting blade only. For example, an alternate cutting element can consist only of cutting blade 122, without blade 124, which would appear identical to cutting element 120 in FIG. 3, but with blade 124 omitted from the Figure. In such a construct, the trocar head 109 could have two branches 129 as shown in FIG. 3, but with no blade 124 on the end of the branch on the right side of the Figure.

Figure 9:
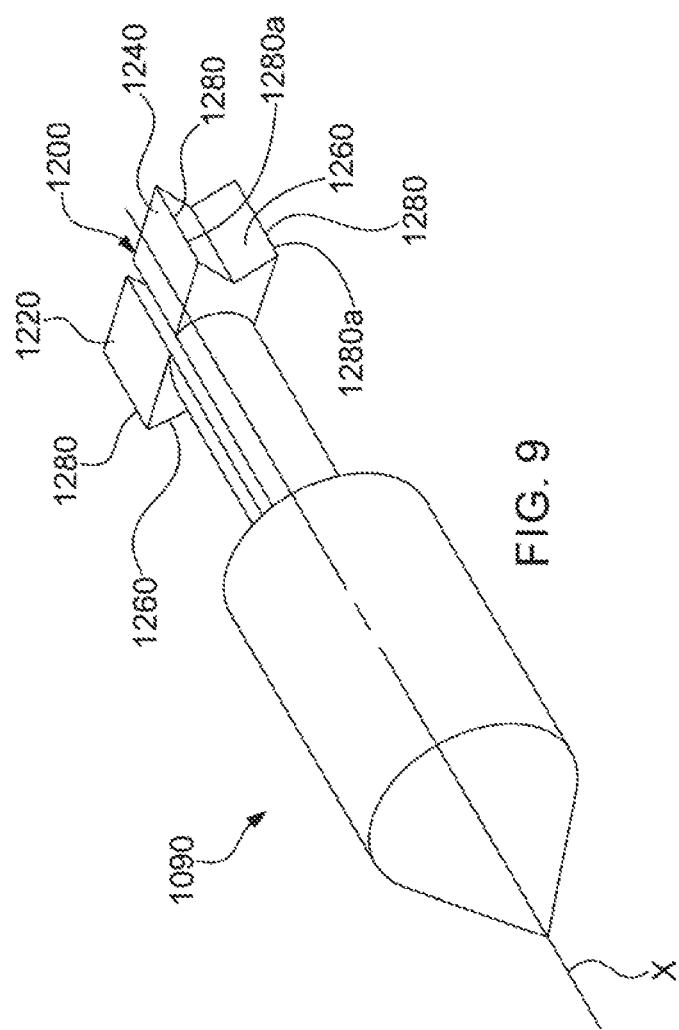
FIG. 9 is a perspective view of a component in accordance with an alternate embodiment of the invention.

Referring now to FIG. 9, an alternate trocar head 1090 is shown. Trocar head 1090 has a cutting element 1200 that is identical to cutting element 120 in many respects, but differs with regard to the orientation of the cutting edges. In particular, cutting element 1200 includes a first blade 1220 and a second blade 1240. First blade 1220 and second blade 1240 each feature a concave cutting face, and in particular a V-shaped cutting face 1260. Each cutting face 1260 comprises cutting teeth 1280 that can cut radially outwardly as well as in an axial direction. Each cutting tooth 1280 defines a linear or substantially linear edge 1280a that extends parallel to longitudinal axis X of trocar head 1090. This parallel orientation of edges 1280a with respect to the longitudinal axis X can be beneficial because it can reduce problems arising from loose bone cuttings. For example, it has been discovered that bone cuttings can sometimes interfere with the retraction of the cutting blades into the trocar. Sometimes bone fragments can prevent the cutting blades from completely retracting into the trocar, such that the cutting edges remain partially projected outside of the apertures and outside the footprint of the trocar distal end. In such cases, the projecting edges can contact and bear against the tunnel wall when the trocar head is pulled out of the tunnel. This can create resistance when the user attempts to withdraw the trocar from the tunnel. In some cases, the projecting edges and/or loose bone can create a jammed condition that prevents the trocar head from being removed from tunnel. Cutting edges that are oriented parallel to the longitudinal axis X of the trocar head, like edges 1280a, can cut through obstructing bone fragments or bone in the event that the edges are not completely retracted into the trocar. In addition, edges that are oriented parallel to the longitudinal axis X of the trocar head like edges 1280a, can cut slightly into the wall of the tunnel when the trocar head is being withdrawn from the tunnel, with little or no resistance. Cutting edges that are oriented parallel to the longitudinal axis X of the trocar head, like edges 1280a, can also create score lines, channels and other surface cuts along a length of the tunnel wall, which can provide additional discontinuities in the tunnel wall for enhancing engagement with and retention of anchors.

As with cutting face 126, the V-shaped profile of cutting face 1260 cuts only a small surface area of the tunnel wall, so there is less surface area to cut. This creates less resistance at the beginning of the cut to make the start of cutting easier. The V-shaped profile also makes it easier to radially expand the cutting face into the bone during cutting, when cutting an enlarged diameter section.

The distal ends of instruments in accordance with the invention have a first cross sectional area that corresponds to the cross sectional area of the tunnel to be formed. The distal ends can have a circular cross section or a non-circular cross section. In this description, cross sections of the tunnel may at times be described as having certain "diameters". Nevertheless, it will be understood that tunnels formed by instruments in accordance with the invention can form circular or non-circular cross sections, as for example in cases where a non-circular piercing tip is tapped into the bone.

Cutting elements in accordance with the invention have a second cross sectional area when partially or fully expanded. The second cross sectional area is wider than the first cross sectional area so that when the cutting elements are rotated in a tunnel formed by the sharpened end, the cutting elements carve out a void or space that surrounds the tunnel. The carved out area is larger in cross section than the cross section of an adjoining section(s) of the tunnel that are not cut by the cutting element. In the case of circular tunnels, the enlarged section will have a radius that is larger than the radius of an adjoining section of the tunnel that is not cut by the cutting element. The dimensions of the tunnel and enlarged section can be selected based on numerous factors, including but not limited to the type of bone anchor being implanted. For example, the maximum diameter of the sharpened tip can be between 1.25 mm and 1.75 mm. A preferable maximum diameter of the sharpened tip might be 1.5 mm. The maximum diameter of the cutting element can be between 1.75 mm and 2.0 mm. A preferable maximum diameter of the cutting element might be 1.8 mm.

The cutting element can be integrated with the trocar in various ways in accordance with the invention. For example, trocars in accordance with the invention can include hollow tubes or cylinders in which the cutting element is housed. The tubes or cylinders can include one or more apertures. Trocar 100 includes a cylindrical hollow shaft or containment tube 140 that includes two diametrically opposed apertures 142. Each aperture is axially and radially aligned with one of the cutting blades 122 and 124. Cutting blades 122 and 124 each extend radially outwardly from a thin flexible leg or branch 129. The branches 129 are attached to piercing tip 112. In the fully assembled state, piercing tip 112 extends outside of hollow shaft 140 and flexible branches 129 extend inside of the hollow shaft. Cutting blades 122 and 124 are also disposed within hollow shaft 140 in a non-deployed state, but are expandable through the apertures to a position outside of the hollow shaft when they are deployed.

Referring to FIG. 3, cutting blades 122 and 124 are separated by a gap 123, and are radially displaceable with respect to the longitudinal axis of trocar 100. In one mode of operation, cutting blades 122 and 124 are radially displaceable away from one another to an expanded position. In another mode of operation, cutting blades 122 and 124 are radially displaceable toward one another to a retracted position. Branches 129 are resilient and flexible. In their relaxed state, branches 129 position cutting blades 122 and 124 in the retracted position. When blades 122 and 124 are expanded, branches 129 are flexed outwardly under stored energy. When the force expanding the blades 122 and 124 is removed, the stored energy is released, and the resiliency of branches 129 returns the blades to the retracted position under a biasing force that urges the blades back to the retracted position.

Blades in accordance with the invention can be expanded using a variety of mechanisms, including springs, cams and other mechanisms. Trocar 100 features a tubular main body 101, and an expansion element in the form of an activation rod 150 that is at least partially housed inside and axially displaceable within the main body. Activation rod 150, also referred to as an activation taper pin, includes a proximal end 152 and a tapered distal end or wedge 154. Wedge 154 is configured to at least partially enter gap 123 between cutting blades 122 and 124 to displace the cutting blades outwardly from the retracted position to the expanded position.

To displace cutting blades 122 and 124 outwardly to the expanded position, activation rod 150 is axially displaced in a distal direction inside main body 101 to advance wedge 154 toward the distal end of trocar 100 and into gap 123. The tapered edge of wedge 154 (or edges in the case of a polygonal shaped wedge) bears against the inside surface of each branch 129 and pushes the branches apart, moving the blades to the expanded position. Activation rods in accordance with the invention can be axially displaced using various mechanisms, including threaded surfaces that convert rotational movement of a knob, sleeve or the like to linear movement of the activation rod. Alternatively, activation rods in accordance with the invention can be axially displaced by elements that impart axial displacement through simple push-pull movements. In trocar 100, an activation sleeve or thimble activator 160 is used to displace activation rod 150. Sleeve 160 is connected to activation rod 150 by a dowel pin 170. Dowel pin 170 is secured by press fitting or other means into a bore 165 in sleeve 160 and a bore 155 in activation rod 150. Dowel pin 170 extends through an elongated slot 103 that extends through the wall of main body 101. Slot 103 is elongated in an axial direction to allow dowel pin 170, and consequently sleeve 160 and activation rod 150, to move through a limited range of motion in an axial direction relative to main body 101. To expand blades 122 and 124, sleeve 160 is moved in a distal direction over main body 101 to advance activation rod 150 into gap 123. To retract blades 122 and 124, sleeve 160 is moved in a proximal direction over main body 101 to withdraw or remove activation rod 150 from gap 123.

Trocars and other instruments in accordance with the invention can be solid tip instruments. Alternatively, trocars and instruments in accordance with the invention can be cannulated; that is, provided with a central bore or passage extending through the entire assembly, for example along the longitudinal axis of the assembly from the proximal-most end to the distal-most end of the assembly. The passage can be sized to receive a guide wire or other guidance device for navigating the instrument to a specific site. In addition, or in the alternative, trocars and other instruments in accordance with the invention can be accompanied by a cannula having an inner diameter larger than the outer diameter of the trocar or instrument. The cannula can be configured for placement through a small percutaneous incision and adapted to receive the trocar or other instrument in accordance with the invention, to guide the trocar or other instrument to a specific surgical site.

Referring to FIGS. 4-8, a procedure for making a tunnel in bone is schematically illustrated in accordance with one possible instrument and method of the invention. The procedure is described as it would be performed using trocar 100. In this example, trocar 100 has a piercing tip and shaft with a maximum diameter of about 1.5 mm to form a tunnel having a diameter of about 1.5 mm. Trocar 100 also has a cutting element 120 that can be expanded radially outwardly to a maximally expanded position in which the outermost cutting edge of the cutting element extends about 0.9 mm away from the longitudinal axis. Thus, cutting element 120 can expand the diameter of the tunnel by about 0.3 mm resulting in an enlarged section having a diameter of about 1.8 mm. While other diameters are contemplated in accordance with the invention, Applicant has found that a tunnel diameter of about 1.5 mm and an enlarged section with a diameter of about 1.8 mm have advantages. These diameters strike an optimum balance between competing objectives, namely: (1) keeping each bone tunnel as small as possible, resulting in less removal of bone; and (2) removing enough bone from each tunnel location to accommodate an anchor of sufficient size and strength to securely hold each tissue anchor in the bone with sufficient pull-out strength.

It will be understood that the described method can be practiced by other types of instruments and embodiments in accordance with the invention. It will also be understood that the illustrated steps do not represent the only possible steps, or the only sequence of steps, that could be used in accordance with the invention. Different steps and combinations thereof are also contemplated in accordance with the invention.

Starting with FIG. 4, a bone is schematically shown with a location or site S, representing the proposed location of a tunnel to be formed in the bone. Site S is selected for receiving a bone anchor, and can be selected along with one or more other nearby sites (not shown), to receive additional bone anchors. All sites are selected in accordance with appropriate medical practices.

Trocar 100 is navigated through overlying tissue (not shown) to the bone using appropriate practices until the piercing tip 112 is located above site S and axially aligned with the desired path or trajectory of the proposed tunnel. If desired, the position of piercing tip 112 can be monitored using various medical imaging techniques to ensure that the tip is in the proper location. Once piercing tip 112 is in the proper position and orientation, the trocar is tapped into the bone. FIG. 4 shows trocar 100 partially tapped into the bone to begin forming a tunnel. Trocar 100 is tapped into the bone until piercing tip reaches the desired depth, which may be predetermined based on factors including but not limited to the type of bone anchor to be used.

The shaft of trocar 100 can include a series of ruler markings 105, with each marking accompanied by a number or other type of indicia. The number or other indicia can represent the distance between the nearby marking and piercing tip 112. In use, this distance would be equivalent to the depth that the piercing tip reaches in the bone. Alternatively, the number or other indicia can represent the distance between the marking and cutting element 120. In use, this distance would be equivalent to the depth that the cutting element reaches in the bone, and consequently, the depth at which the enlarged section would be formed upon activating the cutting element. When tapping the trocar into the bone, markings 105 can also be used to determine how deep the tunnel is beneath the bone surface, and how much more tapping, if any, is required to reach a desired depth.

FIG. 5 shows trocar 100 tapped further into the bone to the desired depth. Upon reaching the desired depth, trocar 100 can be left in place, and the cutting element can be deployed to begin cutting the enlarged section. Alternatively, the position of trocar 100 can be adjusted axially in the tunnel to align the cutting element with the area where an enlarged section is desired. The position of the trocar shaft, and more specifically the position of the cutting element 120, can be monitored with visual imaging, by reference to markings 105 on the trocar, a combination of both, or other methods.

Once cutting element 120 is aligned with the desired location for the enlarged section, activation rod 150 is advanced in the distal direction to drive wedge 154 between the cutting blades 122 and 124. Cutting blades 122 and 124 are pushed radially outwardly through apertures 142 to the position shown in FIG. 6, at which stage the cutting blades are in position to cut an enlarged section. FIG. 7 shows the tunnel with an enlarged section E completed and trocar 100 removed. FIG. 8 shows an all-suture anchor A inserted in the tunnel and deployed, with sutures forming a knot K that is trapped in enlarged section E of the tunnel.

Although the invention is illustrated and described herein with reference to specific embodiments, the invention is not intended to be limited to the details show. Rather, various modifications may be made in the details within the scope and range of equivalents of the claims and without departing from the invention.

What is claimed:

1. A trocar comprising:
a piercing tip;
a cutting element comprising one or more cutting blades;
an expansion element comprising an activation rod for expanding the cutting element radially outwardly with respect to a longitudinal axis of the trocar; and
a hollow shaft,
the one or more cutting blades comprising two opposed cutting blades separated by a gap, the two opposed cutting blades being radially displaceable with respect to the longitudinal axis,
the two opposed cutting blades being radially displaceable away from one another to an expanded position, and radially displaceable toward one another to a retracted position, and
the activation rod comprising a wedge configured to at least partially enter the gap between the two opposed cutting blades to displace the cutting blades to the expanded position;
wherein the activation rod is axially displaceable in the hollow shaft between a distal position, in which the activation rod engages and radially displaces the two opposed cutting blades to the expanded position, and a proximal position, in which the opposed cutting blades are displaced to the retracted position.

2. The trocar of claim 1, wherein the hollow shaft comprises one or more apertures axially and radially aligned with the one or more cutting blades.

3. The trocar of claim 1, wherein the cutting element is at least partially housed in the hollow shaft.

4. The trocar of claim 1, wherein the activation rod is housed inside the hollow shaft in a position proximal to the cutting element.

5. The trocar of claim 1, wherein the two cutting blades are biased toward the retracted position.

6. The trocar of claim 1, wherein each of the two opposed cutting blades comprises a cutting face.

7. The trocar of claim 6, wherein each cutting face comprises a concave-shaped face.

8. The trocar of claim 6, wherein each cutting face comprises a C-shaped face.

9. The trocar of claim 6, wherein each cutting face comprises a V-shaped face.

10. The trocar of claim 6, wherein each cutting face comprises a pair of cutting teeth.

11. The trocar of claim 10, wherein each of the cutting teeth defines an edge that extends parallel to the longitudinal axis of the trocar.

12. The trocar of claim 10, wherein each of the cutting teeth defines an edge that extends perpendicularly to the longitudinal axis of the trocar.

13. The trocar of claim 1, wherein the hollow shaft comprises an end for attaching the trocar to a device for providing torque.

* * * * *